United States Patent [19]

Levy

[11] Patent Number: 4,826,003
[45] Date of Patent: May 2, 1989

[54] VERTICAL PACK COLLECTION KIT

[76] Inventor: Abner Levy, 325 N. Oakhurst Dr. P4, Beverly Hills, Calif. 90210

[21] Appl. No.: 167,990

[22] Filed: Mar. 14, 1988

[51] Int. Cl.$^4$ ............................................. B65D 81/02
[52] U.S. Cl. .................................. 206/45.31; 206/443; 206/523
[58] Field of Search ...................... 206/45.31, 443, 523, 206/568, 569, 570

[56] References Cited

U.S. PATENT DOCUMENTS

| | | | |
|---|---|---|---|
| 2,983,372 | 5/1961 | Amatel et al. | 206/45.31 |
| 3,027,001 | 3/1962 | Herzog | 206/45.31 |
| 3,241,661 | 3/1966 | Zamzow et al. | 206/523 |
| 3,708,061 | 1/1973 | Weingarden et al. | 206/45.31 |
| 4,117,930 | 10/1978 | Pavel | 206/443 |
| 4,240,547 | 12/1980 | Taylor | 206/443 |
| 4,303,153 | 12/1981 | Boulton | 206/45.31 |
| 4,501,360 | 2/1985 | Levy et al. | 206/443 |
| 4,549,659 | 10/1985 | Barnes et al. | 206/443 |

FOREIGN PATENT DOCUMENTS

| | | | |
|---|---|---|---|
| 1410347 | 4/1965 | France | 206/523 |
| 2173174 | 10/1986 | United Kingdom | 206/523 |

*Primary Examiner*—Joseph Man-Fu Moy
*Attorney, Agent, or Firm*—Beehler, Pavitt, Siegemund, Jagger, Martella & Dawes

[57] ABSTRACT

A vertical type kit for tubes containing laboratory specimens of a block of lightweight material of the character of polystyrene in which is molded an array of pockets of assorted sizes and depths for reception of an assortment of tubes, pipettes, fluid containers, and comparable laboratory articles. For those pockets adjacent the edge of the block there are slotted openings which expose the interiors of the pockets and the contents of the pockets. A relatively deep cover fits snugly over the tops of the specimen tubes and when applied to the block leaves portions of the slotted openings exposed.

11 Claims, 1 Drawing Sheet

U.S. Patent   May 2, 1989   4,826,003
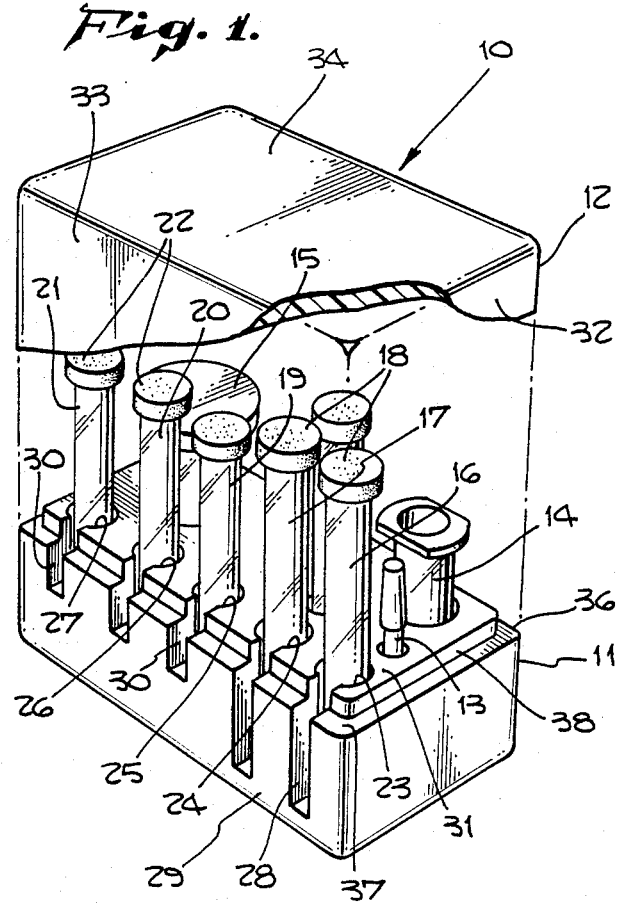
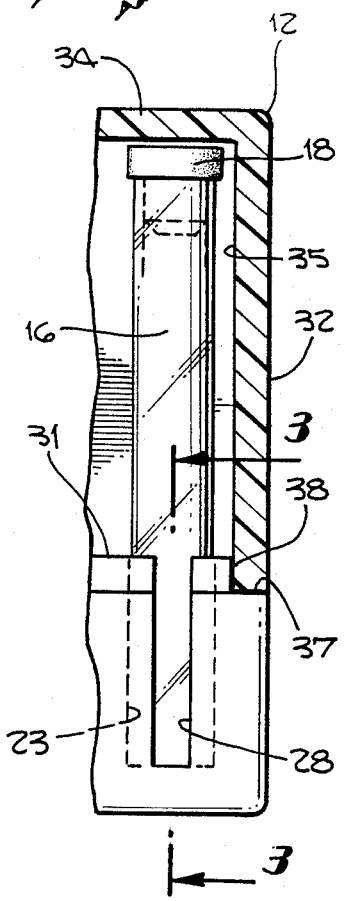
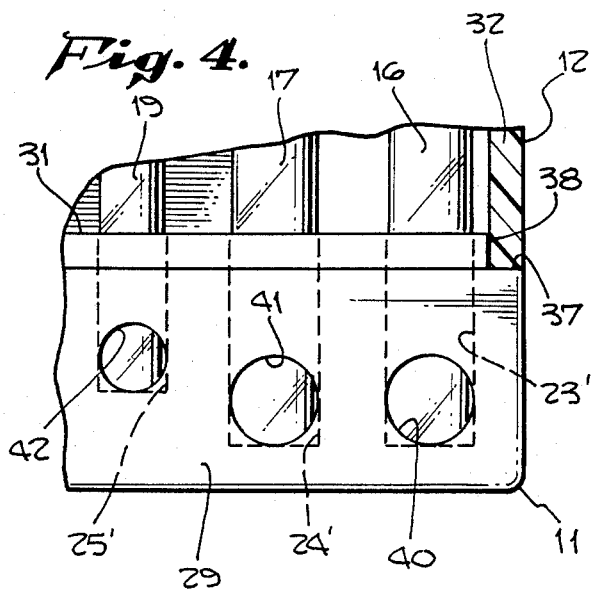
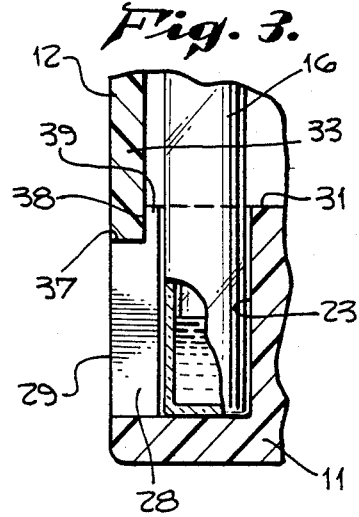

VERTICAL PACK COLLECTION KIT

In the taking and handling of blood and urine specimens, common practice has been to employ a holder of appropriate character in which tubes for the specimens are held upright both before and after specimens have been collected. Although tubes may be effectively sealed with a stopper, it is good practice to continue holding the tubes erect during transportation to the laboratory for analysis and also until the analysis has been made. Quite commonly, where the laboratory may be on the same premises as that of where the specimens are taken, holding the tubes in erect position presents no appreciable problem.

More frequently, in present day practice, there may be many scattered locations where specimens are collected and only one laboratory to serve many such locations. As a consequence, tubes containing specimens must be transported from one place to the other and with the customary care to assure a dependable analysis.

To meet the needs of dependable transportation, resort has been had to shipping containers in which tubes containing specimens for anaylsis can be securely packed. It is, of course, more practical to have such containers have the capacity for accommodating a multiple number of tubes, rather than one or two. Again, as a practical expedient, containers have customarily been set up to contain a supply of empty tubes with stoppers, accompanied by necessary collection paraphernalia such as a sterile needle, alcohol, adhesive patches, and paper forms for identification of the specimens.

Heretofore, flat packs have been the common expedient. Although such flat packs, when made of lightweight Styrofoam provide an effective and safe way to transport tubes of specimens which have been collected, the tubes are, for the most part, handled and stored in a horizontal position. In addition to the horizontal positioning of the tubes being not entirely an acceptable practice, it is always necessary, after unpacking the flat pack, to provide some other equipment to hold the tubes in vertical position after the stopper has been removed and a portion of the specimen taken out for laboratory analysis.

It is therefore among the objects of the invention to provide a new and improved pack for specimen tubes which effectively holds the tubes in a vertical position after being loaded with a specimen.

Another object of the invention is to provide a new and improved means for inspecting the presence of tubes in the pack without opening the pack for such inspection.

Still another object of the invention is to provide a new and improved pack whereby not only the tubes, but the contents also of the tubes, can be inspected without need for opening the pack and removing the tubes.

Still another object of the invention is to provide a new and improved pack wherein there is additionally provided a cover for the pack so positioned that visual inspection of tubes and their contents is not impaired whether the pack be open or closed.

Still another object of the invention is to provide a new and improved pack which greatly facilitates the ease of insertion of tubes in the pack, especially when containing specimens, and also one capable of ease and ready removal when the specimens are to be analyzed.

Still further among the objects of the invention is to provide a new and improved pack which is especially capable of holding tubes containing specimens firmly in vertical position, particularly when being transported from one location to another.

Still further among the objects of the invention is to provide a new and improved pack which provides not only an effectively constituted shipping container for new empty tubes and adequate paraphernelia for collecting specimens but which serves also as an effective shipping container for tubes containing specimens, as well as serving as an appropriate holder for such tubes while the final laboratory analysis is taking place.

Still further among the objects of the invention is to provide a new and improved container which is especially effective in holding in a vertical position tubes which may be of different length and sizes firmly in position during transportation to the laboratory and while specimens are being subjected to laboratory analysis.

With these and other objects in view, the invention consists of the construction, arrangements, and combination of the various parts of the device serving as an example only of one or more embodiments of the invention, whereby the objects contemplated are attained, as hereinafter disclosed in the specification and drawings and pointed out in the appended claims.

In the drawings:

FIG. 1 is a front perspective view of the assembled collection kit partially broken away to reveal the interior.

FIG. 2 is a fragmentary front elevational view.

FIG. 3 is a fragmentary side elevational view taken on the line 3—3 of FIG. 2.

FIG. 4 is a fragmentary front elevational view of a second form of the device.

In one embodiment of the invention chosen for the purpose of illustration, there is shown a collection kit, indicated generally by the reference character 10, consisting essentially of a molded block 11 for holding all of those articles for which the kit is designed and a cover 12. The material of which both the molded block and cover are constructed is preferably of a very lightweight substance such, for example, as commercial Styrofoam which can readily be molded to the desired shape and size.

In the molded block 11 is a pattern of molded openings for what will become the contents of the kit. A typical assortment of contents may be, for example, a conventional needle of the type used to withdraw blood from a punctured blood vessel, a receptacle 14 for the needle, and a covered bottle 15 of a liquid antiseptic in the nature of alcohol. Also included among the contents are two relatively long tubes 16 and 17 supplied with conventional stoppers 18 and three shorter tubes 19, 20 and 21, also provided each with a conventional stopper 22. For accommodation of the sundry receptacles, there is an assortment of pockets molded in the material of the block 11. Pockets, respectively, for the needle 13, the receptacle 14 and bottle 15 have each a diameter sufficient to snugly receive the corresponding article and deep enough to hold the article in its selected position.

In addition to those pockets for the accessory receptacle just made reference to, there are relatively deep tubular pockets 23, 24 for the two relatively long tubes 16 and 17. For the relatively shorter tubes 19, 20 and 21, there are tubular pockets 25, 26, 27 which do not extend as deeply into the material of the block 11.

For the tubular pocket 23, by way of example, there is an inspection opening 28 extending from a front face 29 of the block inwardly into the corresponding tubular pocket. The inspection opening is in the form of a molded slot having a width less than the diameter of the tubular pocket but wide enough to permit visual inspection of the interior of the pocket. In addition to providing for visual inspection of the interior of the pocket, the slotted inspection opening 28 and comparable slotted inspection openings for the other tubular pockets allows a degree of yieldability in that portion of the block so that there is a snug fit between the tubes and the pocket walls to help retain the tubes in place but which, because of the yieldability characteristic, permits ready withdrawal of the tube when needed. For each of the tubular pockets 25, 26, 27 there is a similar inspection opening 30 extending inwardly from the same front face of the block. In this form of the device the inspection openings 28, 30 extend from the bottoms of the respective pockets entirely through the top face 31 of the material of the molded block 11. The cover 12, likewise molded of the same material, is made up of side walls 32, front and rear walls 33, and a top wall 34, the walls forming a relatively deep interior space 35, deep enough to receive in their entirety the exposed portions of all of the tubes and receptacles.

Of special consequence is the fit of the cover 12 on the block 11. To assist in providing the desired fit, there is extending around the entire perimeter of the molded block 11 a step configuration 36 consisting essentially of a land portion 37 and a riser portion 38. The width of the land portion, as note FIG. 2, is substantially the same as the thickness of the side wall 32 of the cover. Built in this manner, there is provided a snug fit between the lowermost rim of the cover 12 and the top of the block 11. The same effective fit of the cover with the step extends throughout the entire perimeter of the block and its cover.

For the relatively long tubes 16 and 17, the corresponding pockets 23, 24 are of a depth such that when the tube 16 is pushed downwardly to the bottom of the tubular pocket 23, the top of the tube will be close to the inside surface of the top wall 34 of the cover, thereby to assure that the tube is held firmly in position. For any one of the relativley shorter tubes 19, 20, 21, the corresponding tubular pocket as, for example, the pocket 25, is made to extend less deeply into the molded block 11 so that when the relatively shorter tube 19 is extended to the bottom of a corresponding pocket, the top of the tube 19 will also be close to the underside of the top wall 34, in that way also to be certain of holding the shorter tube in position in the pocket. Should there, however, be need for making use of still shorter tubes as compared with the long tubes of maximum length, the front wall 34 during the molding operation when the top is formed may be provided with downwardly extending protuberances to a level substantially even with the tops of the shorter tubes, in this way to assure that the tubes are held in upright position in the respective pockets. The same practice may likewise be employed for other articles as, for example, the receptacle 14 or bottle 15. Since the proposed Styrofoam material is extremely light, the additional mass of material needed for the protuberances is negligible.

It is of significance to note that the location of the inspection openings is such that they continue to reveal the interiors of the corresponding tubular pockets not only when the cover is removed, but particularly after the cover has been applied. In this way an operator merely by visual inspection can learn whether or not the package already contains tubes for use in collecting specimens, and also whether or not specimens have actually been collected in the tubes and the cover placed over them. It should further be noted that the tubular pockets as, for example, the pocket 23, is located far enough inwardly from the front face 29 of the block so that there is a portion 39 of the block material remaining between the riser portion 38 and the interior of the pocket, thereby to provide a more rugged construction for that portion of the block on which the various inspection openings are located. Irrespective of what resilience may reside in that portion of the block adjacent the front face 29 by reason of the inspection openings for ease of insertion or withdrawal of the tubes, once the cover has been applied the resilience will be temporarily eliminated and all of the tubes held snugly in position during transportation and until the cover is once again removed.

In the form of device of FIG. 4, inspection openings 40, 41 are provided for tubular pockets 23' and 24'. A similar inspection opening 42 accommodates the tubular pocket 25'. On this occasion the inspection openings are cylindrical passageways which extend from the front face 29 of the block 11 inwardly into the interiors of the corresponding tubular pockets. The inspection openings are located adjacent the bottoms of the tubular pockets so that they remain clear at all times both before and after the cover 12 has been applied.

While particular embodiments of the present invention have been shown and described, it will be obvious to those skilled in the art that changes and modifications may be made without departing from the invention in its broader aspects, and therefore, the aims of its appended claims are to cover all such changes and modificatios as fall within the true spirit and scope of this invention.

Having described the invention, what is claimed as new in support of Letters Patent is as follows:

1. A kit for containment of receptacles of tubular form in vertical position comprising a molded block of light-weight material of the character of Styrofoam having exposed bottom, top and side faces, an array of pre-formed tubular pockets extending from the top face into and part-way through the material of the block, at least some of said pockets being adjacent a side face, means forming inspection openings between the side face and the interiors of adjacent pockets and a cover for said block having side and top walls forming a hollow interior with an open bottom for containment of exposed portions of said receptacles when the cover is in closed position on said block, positioning means respectively on the block and the side wall of the cover adapted to hold the cover in position on the block, said positioning means on the block comprising a step structure with a land portion extending from the side face inwardly of the block and a riser portion extending from the land portion to the top face.

2. A kit for containment of receptacles as in claim 1 wherein the block is of solid substantially opaque material and the cover is of relatively stiff opaque material.

3. A kit for containment of receptacles as in claim 1 wherein when the cover is in a closed position on said block at least a portion of the area of said openings is exposed to the exterior.

4. A kit for containment of receptacles as in claim 1 wherein said openings are slots extending from the top face of the block throughout substantially the depths of said pockets.

5. A kit for containment of receptacles as in claim 1 wherein said array of tubular pockets comprises individual pockets of various cross-sectional areas and depths extending throughout the area of said top face and inwardly relative to the side faces.

6. A kit for containment of receptacles as in claim 1 wherein outermost portions of said pockets are located inwardly relative to the location of said riser portion.

7. A kit for containment of receptacles as in claim 1 wherein positioning means for the cover comprises side wall portions having a shape and size complementary to the land and riser portions of the block.

8. A kit for containment of receptacles as in claim 1 wherein said kit includes receptacles of different lengths and wherein the distance between the bottom of the pockets and the inside surface of the top wall of the cover at a corresponding location is substantially the same as the length of the corresponding receptacles when the cover is in said closed position on the block.

9. A kit for containment of receptacles as in claim 1 wherein said kit includes receptacles of different lengths and the depth of the tubular pockets for receptacles of lesser length is less than the depth for receptacles of greater length whereby tops of the receptacles when in place are in substantially the same plane.

10. A kit for containment of receptacles as in claim 1 wherein said cover has an array of pockets with pockets of said array at locations corresponding to locations of pockets in said block whereby to contain portions of said receptacles not contained in pockets of the block.

11. A kit for containment of receptacles as in claim 1 wherein said kit includes receptacles for reception in said pockets and said top wall of the cover has inside face portions at locations substantially in the same plane as tops of the receptacles at corresponding locations whereby to confine said receptacles to positions in the corresponding pockets.

* * * * *